US012685701B2

(12) United States Patent
Bichon et al.

(10) Patent No.: US 12,685,701 B2
(45) Date of Patent: Jul. 21, 2026

(54) COSMETIC MAKE-UP COMPOSITION WITH LONG-LASTING SKIN-PERFECTING EFFECT

(71) Applicant: L V M H RECHERCHE, Saint Jean de Braye (FR)

(72) Inventors: Yohann Bichon, Saint-Jean de Braye (FR); Leïla Azzaz, Orleans (FR)

(73) Assignee: L V M H RECHERCHE, Saint-Jean de Brave (FR)

( * ) Notice: Subject to any disclaimer, the term of this patent is extended or adjusted under 35 U.S.C. 154(b) by 680 days.

(21) Appl. No.: 17/295,571

(22) PCT Filed: Nov. 20, 2019

(86) PCT No.: PCT/EP2019/081882

§ 371 (c)(1),
(2) Date: May 20, 2021

(87) PCT Pub. No.: WO2020/104502

PCT Pub. Date: May 28, 2020

(65) Prior Publication Data

US 2022/0016012 A1 Jan. 20, 2022

(30) Foreign Application Priority Data

Nov. 20, 2018 (FR) ...................................... 1871615

(51) Int. Cl.

| | |
|---|---|
| ***A61K 8/58*** | (2006.01) |
| ***A61K 8/06*** | (2006.01) |
| ***A61K 8/81*** | (2006.01) |
| ***A61Q 1/02*** | (2006.01) |

(52) U.S. Cl.

CPC .............. *A61K 8/585* (2013.01); *A61K 8/064* (2013.01); *A61K 8/8176* (2013.01); *A61K 8/8182* (2013.01); *A61Q 1/02* (2013.01); *A61K 2800/43* (2013.01)

(58) Field of Classification Search

CPC .... A61K 2800/43; A61K 8/064; A61K 8/585; A61K 8/8176; A61K 8/8182; A61K 8/891; A61K 8/895; A61K 8/892; A61Q 1/02

See application file for complete search history.

(56) References Cited

U.S. PATENT DOCUMENTS

| | | | | |
|---|---|---|---|---|
| 5,538,793 | A | 7/1996 | Inokuchi et al. | |
| 6,326,013 | B1 | 12/2001 | Lemann et al. | |
| 2004/0170586 | A1* | 9/2004 | Ferrari | A61Q 19/00 424/63 |
| 2011/0110992 | A1* | 5/2011 | Garrison | A61K 8/8152 424/401 |
| 2017/0281521 | A1* | 10/2017 | El-Khouri | A61K 8/60 |

FOREIGN PATENT DOCUMENTS

| | | | |
|---|---|---|---|
| EP | 0987012 | A1 | 3/2000 |
| EP | 1 616 557 | A2 | 1/2006 |
| JP | 2006-28177 | A | 2/2006 |

OTHER PUBLICATIONS

Mintel., "Multi-Prefection Makeup Base SPF 25" Feb. 28, 2013. Extract from www.gnpd.com, Database accession No. 1053151.
Mintel., "Leave-In Serum" Jun. 3, 2008. Extract from www.gnpd.com, Database accession No. 1053151.
International Search Report and Written Opinion for corresponding International Application No. PCT/EP2019/081882, mailing date Jan. 24, 2020.
Preliminary Search Report issued for French Application No. 1871615, dated Jun. 13, 2019.
OECD/OCDE "OECD Guidelines for the Testing of Chemicals—Vapour pressure", (No. 104 adopted on Mar. 23, 2006).
Korean Office Action for Korean Application No. 10-2021-7018022, dated Dec. 16, 2024, with English translation.

* cited by examiner

*Primary Examiner* — Jeffrey T. Palenik
(74) *Attorney, Agent, or Firm* — Birch, Stewart, Kolasch & Birch, LLP

(57) ABSTRACT

The present invention concerns a cosmetic make-up composition for keratinous materials, in particular the skin, in the form of an emulsion, comprising, in a physiologically acceptable medium, at least one phenylated silicone oil of formula (I), a fat-soluble film-forming polymer, a water-soluble film-forming polymer selected from vinylpyrrolidone homopolymers and copolymers, and colouring materials.

9 Claims, No Drawings

COSMETIC MAKE-UP COMPOSITION WITH LONG-LASTING SKIN-PERFECTING EFFECT

CROSS REFERENCE TO RELATED APPLICATIONS

This application is a U.S. National Stage of International Patent Application No. PCT/EP2019/081882 filed Nov. 20, 2019, which claims the benefit of priority of French Patent Application No. 1871615 filed Nov. 20, 2018, the respective disclosures of which are each incorporated herein by reference in their entireties.

BACKGROUND

Field of the Invention

The present invention relates to cosmetic skin make-up compositions imparting a long-lasting skin-perfecting effect and a natural glow to the complexion.

State of the Art

Skin make-up compositions, in particular foundations, have been used for many years to improve the aesthetic appearance of the skin by reducing, among other things, visible and/or tactile irregularities of the skin. Today, consumers are looking for comfortable, lighter galenic formulations with a natural make-up result, but without compromising on the make-up result (covering but natural) and its wear over time (preferably 24-hour wear). In the prior art, foundations are known to be used in the form of water-in-oil emulsions comprising silicone oils and hydrophobic treated pigments for good adhesion to the skin, and film-forming polymers to improve the wear of the deposit, but there is still a need to develop new compositions with a long-lasting skin-perfecting effect and a natural glow to the complexion. The person skilled in the art has at his or her disposal multiple alternatives for achieving this result, by adjusting the nature of the constituent ingredients of the composition, in particular the nature of the fillers, pigments, oils and/or film-forming polymers.

However, the Applicant has shown that the use of a particular phenylated silicone oil, trimethyl pentaphenyl trisiloxane, compared with other silicone or hydrocarbon gloss oils, in a composition in the form of an emulsion comprising oils, film-forming polymers and colouring materials, makes it possible to achieve this natural complexion radiance performance without compromising either the make-up result (natural coverage) or the cosmetic properties of its deposit (non-sticky and long-lasting deposit).

DISCLOSURE OF THE INVENTION

A first object of the invention is therefore a cosmetic make-up composition for keratinous materials, in particular the skin, in the form of an emulsion, comprising, in a physiologically acceptable medium, at least:

a) A phenylated silicone oil of formula (I)

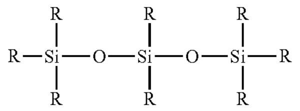

in which the groups R independently represent a methyl or a phenyl, at least three of them, indeed at least four of them, indeed at least five of them being a phenyl, b) A fat-soluble film-forming polymer, preferably a silicone film-forming polymer, c) A water-soluble film-forming polymer selected from homo- and copolymers of vinylpyrrolidone, and (d) Colouring materials, preferably pigments.

The invention also relates to a cosmetic make-up method for keratinous materials, in particular the skin, preferably the skin of the face and/or neck, comprising applying to said keratinous material at least one cosmetic composition as defined according to the invention.

The process is in particular designed to give the skin a long-lasting skin-perfecting effect and a natural glow to the complexion.

According to the invention, 'skin-perfecting effect' means an improvement in the aesthetic appearance of the skin, in particular a reduction in the visible and/or tactile irregularities of the skin.

According to the invention, 'long-lasting skin-perfecting effect' means that this effect is maintained for a period ranging from 12 h to 24 h, and better still for a period of 24 h.

According to the invention, 'natural glow to the complexion' means a fresh and luminous complexion, a healthy glow effect, without a mask effect. The terms 'glow' or 'healthy glow' effect are also used to characterize this naturally radiant skin tone.

DETAILED DESCRIPTION OF THE INVENTION

The invention therefore relates in particular to a cosmetic make-up composition for keratinous materials, in particular the skin, in the form of an emulsion, comprising, in a physiologically acceptable medium, at least:

a) A phenylated silicone oil of formula (I)

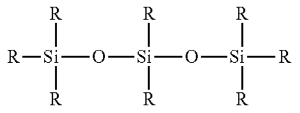

in which the groups R independently represent a methyl or a phenyl, at least three of them, indeed at least four of them, indeed at least five of them being a phenyl, b) A fat-soluble film-forming polymer, preferably a silicone film-forming polymer, c) A water-soluble film-forming polymer selected from homo- and copolymers of vinylpyrrolidone, and (d) Colouring materials, preferably pigments.

The cosmetic composition of the invention is advantageously in the form of an oil-in-water emulsion, a water-in-oil emulsion, a water-in-silicone emulsion, a silicone-in-water emulsion, or a multiple emulsion, for example a triple emulsion.

According to a particular and preferred embodiment, the composition of the invention is a water-in-oil emulsion, in particular a water-in-silicone emulsion.

Oil Phase

The composition of the invention comprises at least one oil phase.

"Oil phase" means an oil or a mixture of mutually miscible oils.

In the context of the invention, "oil" means a fatty substance which is not soluble in water and which is liquid at 25° C. and atmospheric pressure.

An oil phase according to the invention may comprise hydrocarbon, silicone, fluorinated or non-fluorinated oils and mixtures thereof. Preferably, the composition of the invention comprises at least silicone oils.

These oils can be volatile or non-volatile, vegetable, mineral or synthetic.

According to a particular and preferred embodiment, it comprises at least one mixture of volatile oils and non-volatile oils.

According to the invention, 'volatile oil' means an oil of a volatile nature defined by at least one of the criteria defined below.

The volatility may be defined within the context of the invention by, for example, a vapour pressure measurable at 25° C. by an empirical method, the value of which will be between 2.6 Pa and 40 000 Pa, for example between 5 Pa and 20 000 Pa, between 10 Pa and 8 000 Pa, indeed between 15 and 150 Pa. The vapour pressure will be measured according to one of the most suitable methods for the compound of interest, in particular according to the method recommended by the document "OECD Guidelines for the Testing of Chemicals-Vapour pressure", (no. 104 adopted on 23 Mar. 2006). Alternatively, a volatile oil may be selected which has a boiling temperature at atmospheric pressure below 250° C., preferably below 230° C. and preferably between 150° C. and 220° C. Finally, the volatile oil may also be defined as an oil having a flash point ranging from 35° C. to 100° C., preferably between 40° C. and 80° C.

According to the invention, 'non-volatile oil' means an oil which does not meet the volatility criteria defined above, in particular an oil having a vapour pressure, measurable at 25° C. by an empirical method, of less than 2.6 Pa, preferably less than 0.13 Pa, measured in particular by the method described above.

According to the invention, 'hydrocarbon oil' means an oil containing mainly hydrogen and carbon atoms.

According to the invention, "silicone oil" means an oil comprising at least one silicon atom, and in particular at least one Si—O group.

According to the invention, "fluorinated oil" means an oil comprising at least one fluorine atom.

The oils may be present in the composition of the invention in a content ranging from 10 to 80% by weight based on the total weight of the composition. In the remainder of the description, the oil contents indicated, whether as non-volatile oils or as volatile oils, also take into account the contents of oils present in raw materials as solvents, for example for dispersing compounds such as gelling agents, film-forming polymers, and pigments.

Non-Volatile Oils

As non-volatile hydrocarbon oils, particular mention may be made of hydrocarbon oils, hydrocarbon oils of vegetable origin, synthetic $C_{10}$-$C_{40}$ ethers, synthetic $C_{10}$-$C_{40}$ esters, $C_{12}$-$C_{26}$ fatty alcohols, $C_{12}$-$C_{22}$ higher fatty acids, and mixtures thereof.

As non-volatile silicone oils, particular mention may be made of phenylated silicone oils, non-phenylated silicone oils and mixtures thereof.

Phenylated Silicone Oil

The composition of the invention comprises at least one phenylated silicone oil. According to the invention, "phenylated silicone oil" is understood to mean an organopolysiloxane substituted by at least one phenyl group.

The composition of the invention comprises at least one phenylated silicone oil of formula (I)

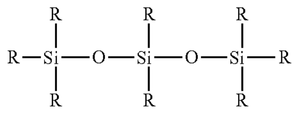

in which the groups R independently represent a methyl or a phenyl, at least three of them, indeed at least four of them, indeed at least five of them being a phenyl.

According to a particular and preferred embodiment, the composition of the invention comprises a phenylated silicone oil of formula (II)

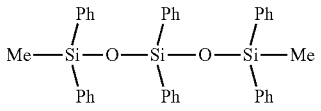

in which Me represents a methyl and Ph represents a phenyl, otherwise named trimethyl pentaphenyl trisiloxane.

Such a phenylated silicone is notably manufactured by Dow Corning under the product code PH-1555 HRI® or Dow Corning 555 Cosmetic Fluid® (chemical name: 1,3,5-trimethyl 1,1,3,5,5-pentaphenyl trisiloxane, INCI name: trimethyl pentaphenyl trisiloxane). Dow Corning product code 554 Cosmetic Fluid® may also be used. According to a preferred embodiment, product code PH-1555 HRI® (INCI name: trimethyl pentaphenyl trisiloxane) is used.

The silicone oil of formula (I) or of formula (II) according to the invention will be present in the composition of the invention in a content ranging from 1 to 12% by weight, preferably from 3 to 8% by weight based on the total weight of said composition.

Additional Phenylated Silicone Oil

Advantageously, the composition of the invention further comprises a second phenylated silicone oil, distinct from the first silicone oil of formula (I) or (II), and selected in particular from the group consisting of phenyl trimethicones phenyl dimethicones, phenyl trimethylsiloxy diphenylsiloxanes, diphenyl dimethicones, diphenyl methyldiphenyl trisiloxanes, 2-phenylethyl trimethylsiloxysilicates, and mixtures thereof, preferably a phenyl trimethicone.

The content of additional phenylated silicone oil may range from 1 to 12% by weight, in particular from 2 to 8% by weight based on the total weight of said composition.

Other Additional Non-Volatile Oils

The composition of the invention may further comprise other non-volatile, hydrocarbon or silicone oils.

The additional non-volatile silicone oils which can be used in the composition according to the invention can be non-volatile polydimethylsiloxanes (PDMS), polydimethylsiloxanes containing at least one $C_{2-24}$ alkyl or alkoxy group, pendant and/or at the end of the silicone chain, phenylated silicones such as phenyl trimethicones, phenyl dimethicones, phenyl trimethylsiloxy diphenylsiloxanes, diphenyl dimethicones, diphenyl methyldiphenyl trisiloxanes, 2-phenylethyl trimethylsiloxysilicates.

The total content of non-volatile oils in the composition of the invention will generally range from 5 to 20% by weight, preferably from 10 to 15% by weight based on the total weight of the composition.

Volatile Oils

According to a particular and preferred embodiment, the composition of the invention further comprises one or more volatile oils, preferably in a total content ranging from 10 to 30% by weight, preferably from 15 to 25% by weight based on the total weight of said composition.

The high level of volatile phase, and in particular volatile oils, makes it possible to have a light composition which is easy to apply to the skin; the volatile oils help to set up the film on the skin during application, and when they evaporate, they leave the film adhering to the skin, with a sensation of bare skin, without any material effect or mask effect on the skin.

The volatile phase of the composition, which comprises in particular water, $C_1$-$C_5$ monoalcohols and volatile oils, will advantageously represent from 30 to 70% by weight, in particular from 40 to 60% by weight, and preferably from 45 to 55% by weight of the total weight of the composition.

As volatile hydrocarbon oils, mention may be made of branched $C_8$-$C_{16}$ alkanes, branched $C_8$-$C_{16}$ esters and mixtures thereof.

As volatile silicone oils, mention may be made of linear or cyclic volatile silicone oils and mixtures thereof.

The volatile oils which are used in the composition of the invention are preferably volatile silicones or branched-chain saturated hydrocarbons.

The volatile oil may in particular be selected from silicone oils such as dimethicones (polydimethylsiloxanes) having a viscosity ranging from 0.5 to 6 cSt, alkyl trisiloxanes and cyclomethicones. Mention will be made, for example, of octamethyl cyclotetrasiloxane, decamethyl cyclopentasiloxane, dodecamethyl cyclohexasiloxane, hexamethyl disiloxane, heptamethyl hexyltrisiloxane, heptamethyloctyl trisiloxane, octamethyl trisiloxane, 1,1,1,3,5,5,5-Heptamethyl-3-(trimethylsiloxy)trisiloxane (otherwise known as methyl trimethicone), decamethyl tetrasiloxane, dodecamethyl pentasiloxane, and mixtures thereof.

According to a particular and preferred embodiment, the composition of the invention comprises at least one volatile silicone oil selected from dimethicones having a viscosity ranging from 0.5 to 6 cSt, methyl trimethicone and mixtures thereof.

The volatile hydrocarbon oil may be iso-hexyl neopentanoate or a hydrocarbon such as isododecane, isodecane, isohexadecane, n-dodecane ($C_{12}$) and n-tetradecane ($C_{14}$) or mixtures thereof.

According to a particular embodiment, the composition of the invention comprises at least isododecane.

According to a particular and preferred embodiment, the composition of the invention comprises at least two volatile silicone oils (5 cSt dimethicone and methyl trimethicone) and a volatile hydrocarbon oil (isododecane).

The content of volatile silicone oils in the composition of the invention will generally range from 10 to 35% by weight, preferably from 15 to 30% by weight based on the total weight of the composition.

The content of volatile hydrocarbon oils in the composition of the invention may range from 2 to 20% by weight, preferably from 5 to 12% by weight based on the total weight of the composition.

According to a particular and preferred embodiment, the composition of the invention will comprise a weight ratio of volatile oils to non-volatile oils ranging from 1 to 3, preferably from 1.5 to 2.5.

Fat-Soluble Film-Forming Polymer

The composition of the invention further comprises a fat-soluble film-forming polymer.

Film-forming polymer means a polymer capable of forming a continuous film on a support. In the text, the word polymer may designate a homopolymer or a copolymer. "Copolymer" means a polymer comprising at least two different monomers or blocks, which may be of the same chemical family but different in structure. Fat-soluble film-forming polymer means a film-forming polymer solubilized in the liquid fat phase, for example in the phenylated silicone oil according to the invention.

The film-forming polymer may be of natural or synthetic origin, and is advantageously selected from the group consisting of:

- trimethylsiloxysilicates,
- phenylalkylsiloxysilicates in which the alkyl group preferably comprises from 1 to 6 carbon atoms, such as phenylpropyldimethylsiloxysilicate,
- silicone acrylate polymers such as acrylate/dimethicone copolymers, and in particular acrylate/dimethicone copolymers in cyclopentasiloxane (such as for example KP-545® from Shin-Etsu), acrylate/dimethicone copolymers in methyl trimethicone (such as for example KP-549® and KP-579® from Shin-Etsu), and acrylate/dimethicone copolymers in isododecane (such as for example KP-550® from Shin-Etsu); acrylate/polytrimethylsiloxy-methacrylate copolymers, and in particular acrylate/polytrimethylsiloxy-methacrylate copolymers in dimethicone (such as for example Dow Corning® FA-4003 DM®), acrylate/polytrimethylsiloxy-methacrylate copolymers in isododecane (such as for example Dow Corning® FA-4004 ID®)
- polyalkylsilsesquioxanes comprising 1 to 6 carbon atoms, and preferably polymethylsilsesquioxane (such as for example Silform® Flexible Resin from Momentive),
- trialkylsiloxysilylcarbamoyl pullulans in which the alkyl group comprises from 1 to 6 carbon atoms, and preferably trimethylsiloxysilylcarbamoyl pullulan (such as for example TSPL-30-ID from Shin-Etsu),
- copolymers of vinylpyrrolidone (VP) and alkene comprising from 2 to 20 carbon atoms, such as copolymers of VP/eicosene, VP/hexadecene, VP/styrene,
- fat-soluble copolymers of a vinyl ester, and preferably vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/octadecene-1, vinyl acetate/dodecene-1, vinyl stearate/ethyl vinyl ether, vinyl propionate/acetyl vinyl ether, vinyl stearate/allyl acetate, vinyl dimethyl-2,2-octanoate/vinyl laurate, allyl dimethyl-2,2-pentanoate/vinyl laurate, vinyl dimethyl propionate/vinyl stearate, allyl dimethyl propionate/vinyl stearate,
- polyolefins, hydrogenated or non-hydrogenated, and preferably polymers or copolymers of alkenes comprising from 2 to 20 carbon atoms, such as polybutenes, polyisobutenes and polydecenes,
- alkylcelluloses, and preferably alkylcelluloses carrying an alkyl group comprising from 2 to 6 carbon atoms, such as ethylcellulose and propylcellulose,
- polyvinyl alcohols, and
- mixtures thereof.

Preferably, the fat-soluble film-forming polymer is a silicone film-forming polymer selected from the group consisting of:

- trimethylsiloxysilicates,
- phenylalkylsiloxysilicates in which the alkyl group preferably comprises from 1 to 6 carbon atoms, such as phenylpropyldimethylsiloxysilicate,

- silicone acrylate polymers such as acrylate/dimethicone copolymers, and in particular acrylate/dimethicone copolymers in cyclopentasiloxane (such as for example KP-545® from Shin-Etsu) acrylate/dimethicone copolymers in methyl trimethicone (such as for example KP-549® and KP-579® from Shin-Etsu), and acrylate/dimethicone copolymers in isododecane (such as for example KP-550® from Shin-Etsu); acrylate/polytrimethylsiloxy-methacrylate copolymers, and in particular acrylate/polytrimethylsiloxy-methacrylate copolymers in dimethicone (such as for example Dow Corning® FA-4003 DM®), acrylate/polytrimethylsiloxy-methacrylate copolymers in isododecane (such as for example Dow Corning® FA-4004 ID®)
- polyalkylsilsesquioxanes comprising from 1 to 6 carbon atoms, and preferably polymethylsilsesquioxane (such as for example Silform® Flexible Resin from Momentive),
- trialkylsiloxysilylcarbamoyl pullulans in which the alkyl group comprises from 1 to 6 carbon atoms, and preferably trimethylsiloxysilylcarbamoyl pullulan (such as for example TSPL-30-ID® from Shin-Etsu),
- and mixtures thereof.

Even more preferably, the fat-soluble film-forming polymer b) is selected from trimethylsiloxysilicates, silicone acrylate polymers and mixtures thereof.

According to a particular and preferred embodiment, the composition of the invention comprises at least one silicone acrylate polymer, in particular selected from acrylate/dimethicone copolymers in methyl trimethicone (such as for example KP-549® and KP-579® from Shin-Etsu).

The fat-soluble film-forming polymer b) is present in a content ranging from 1 to 7% by weight, preferably from 2 to 5% by weight based on the total weight of said composition. The % of fat-soluble film-forming polymer b) is expressed as % by weight of dry extract (active material, a.m.) based on the total weight of the composition.

Aqueous Phase

The aqueous phase of the composition according to the invention generally represents from 1 to 80% by weight, in particular from 20 to 60% by weight, based on the total weight of said composition.

The aqueous phase comprises water and optionally a water-soluble solvent.

According to the invention, "water-soluble solvent" means a compound which is liquid at room temperature and miscible with water (miscibility in water greater than 50% by weight at 25° C. and atmospheric pressure). Particular mention may be made of:

- lower $C_1$-$C_5$ monoalcohols such as ethanol, isopropanol and mixtures thereof, preferably ethanol;
- $C_2$-$C_8$ glycols such as ethylene glycol, propylene glycol, 1,3-butylene glycol, dipropylene glycol, and mixtures thereof;
- $C_2$-$C_{32}$ polyols such as glycerol, polyglycerols, polyethylene glycols, and mixtures thereof, and mixtures thereof.

Thus, a cosmetic composition according to the invention further comprises at least one water-soluble solvent selected from $C_1$-$C_5$ lower monoalcohols, $C_2$-$C_8$ glycols, $C_2$-$C_{32}$ polyols, and mixtures thereof, preferably in a total content ranging from 10 to 25% by weight, in particular from 15 to 20% by weight based on the total weight of said composition.

According to a particular and preferred embodiment, the composition of the invention will comprise at least ethanol, preferably in a content ranging from 5 to 15% by weight based on the total weight of the composition, imparting a fresh effect.

And the composition will advantageously further comprise at least polyols and/or glycols in a total content ranging from 3 to 12% by weight, in particular 5 to 10% by weight based on the total weight of the composition, for a moisturizing effect promoting a radiant complexion ('glowy' effect) without an oily effect.

Water-Soluble Film-Forming Polymer

The composition of the invention comprises a water-soluble film-forming polymer.

The water-soluble film-forming polymers are soluble in the aqueous or hydroalcoholic phase of the composition of the invention. In particular, soluble means that it is possible to dissolve the polymer in an alcoholic or aqueous solvent, at room temperature, and at a percentage by weight generally less than or equal to 80%. According to an embodiment, the water-soluble film-forming polymer according to the invention is selected from the group consisting of vinyl polymers, polyacrylates, polyurethanes and mixtures thereof.

In particular, the water-soluble film-forming polymer c) according to the invention is selected from vinylpyrrolidone homo- and copolymers, and mixtures thereof.

Among homopolymers, mention may be made of polyvinylpyrrolidones (PVP) of different molecular weights, the weight-average molecular weight of said homopolymer being measured by light diffraction. More particularly the polyvinylpyrrolidones (PVP) are selected from polyvinylpyrrolidones having a weight-average molecular weight ranging from 2000 daltons to 3000000 daltons, more particularly having a weight-average molecular weight ranging from 30000 daltons to 2000000 daltons, preferably having a weight-average molecular weight ranging from 40000 daltons to 1500000 daltons.

In another embodiment of the invention, any type of water-soluble vinylpyrrolidone copolymer may be used. Here, copolymer means both polymers resulting from the polymerization of vinylpyrrolidone with a single kind of monomer and those resulting from the polymerization of vinylpyrrolidone with several kinds of monomers, and for example with two kinds of monomers leading to the obtaining of terpolymer.

Among the water-soluble copolymers of vinylpyrrolidone, advantageous mention may be made of:

- copolymers comprising at least the vinylpyrrolidone and vinyl acetate monomers, such as polyvinylpyrrolidone/vinyl acetate (PVP/VA), polyvinylpyrrolidone/vinyl acetate/itaconic acid, polyvinylpyrrolidone/vinyl acetate/vinyl propionate copolymers,
- polyvinylpyrrolidone/(meth)acrylic acid/$C_8$-$C_{20}$ alkyl methacrylate copolymer, in particular lauryl, By way of example, a polyvinylpyrrolidone in accordance with the invention is available under the trade name PVP-K® or PVPNA® such as PVP K 30L® or PVP K 90®, from the company ISP.

Examples of vinyl acetate copolymers that may be suitable are commercially available under the brand names PVP/VA 6-630® (International Specialty Products) or PVP-VA S-630® by Ashland Specialty Chemical (INCI name: vinylpyrrolidone/vinyl acetate copolymers or VP/VA COPOLYMER®, and chemical name: poly(vinylpyrrolidone-co-vinyl acetate). PLASDONE S-630™ VP/VA copolymer is a linear copolymer of N-vinyl-2-pyrrolidone (PVP) and vinyl acetate in a 60:40 ratio.

In particular, the water-soluble film-forming polymer c), in particular selected from vinylpyrrolidone/vinyl acetate (PVP/VA) copolymers, is present in a content ranging from 0.05 to 2% by weight, preferably from 0.1 to 1% by weight based on the total weight of the composition. The % of water-soluble film-forming polymer c) is expressed as % by weight of dry extract (active material, a.m.) based on the total weight of the composition.

Fillers

The composition of the invention may further comprise at least one filler, preferably a soft-focus effect filler.

In the context of the invention, "fillers" are to be understood as colourless or white particles, of mineral or organic, natural or synthetic nature, which are in an insoluble form and dispersed in the medium of the composition. The fillers according to the invention may or may not be surface-coated and, in particular, they may be surface-treated with silicones, amino acids, fluorine-based derivatives or any other substance which promotes the dispersion and compatibility of the filler in the composition.

The fillers are selected in particular from silicas, micas, of natural or synthetic origin, kaolin, zinc and titanium oxides; calcium carbonate, magnesium carbonate and magnesium hydrocarbonate; zinc, magnesium or lithium stearate, zinc laurate, magnesium myristate; synthetic polymer powders, such as polyethylene, polyesters, polyamides (for example nylon); powders of polyacrylic or polymethacrylic acid, powders of silicone resin; mineral powders such as spherical silica; spherical titanium dioxides; glass and ceramic beads; powders of organic materials of natural origin such as maize, wheat, rice starches, cross-linked or not, and mixtures thereof.

The composition according to the invention will advantageously comprise at least one soft-focus effect filler. In the sense of the invention, 'soft-focus effect' means an effect which camouflages the microrelief of the skin and thus makes it possible to attenuate, by optical correction effect, the imperfections of relief and/or of colour, such as wrinkles, fine lines, pores and spots.

In the remainder of the description, the terms 'soft-focus effect filler or 'soft-focus filler' are used interchangeably.

As 'soft-focus effect fillers' according to the invention, advantageous mention may be made of the fillers selected from the group consisting of: cellulose powders, cellulose beads; microcrystalline cellulose powders; silica and silicate powders, amorphous silica microspheres, silica microbeads; silica/$TiO_2$ composite powders; talc/$TiO_2$/alumina/silica composite powders; polymethyl methacrylate (PMMA) powders; boron nitride powders; cross-linked elastomeric organopolysiloxane powders optionally coated with silicone resin; hydrophobic silica aerogel powders; nylon powders; starch powders; powders of vegetable origin, such as rice powders, cotton powders, silk powders; and mixtures thereof.

According to a preferred embodiment of the invention, the cosmetic composition comprises at least one soft-focus effect filler selected from the group consisting of polymethyl methacrylate (PMMA) powders, crosslinked elastomeric organopolysiloxane powders optionally coated with silicone resin, and mixtures thereof. As polymethyl methacrylate (PMMA) powders, particular mention may be made of the powders with the INCI name "methylmethacrylate crosspolymer", such as SUNPMMA-X® from the company Sunjin or MAKIBEADS 150® from the company Daito Kasei.

As silicone resin-coated crosslinked elastomeric organopolysiloxane powders, mention may be made of silsesquioxane resin-coated crosslinked elastomeric organopolysiloxane powders, as described for example in the patent U.S. Pat. No. 5,538,793. Such elastomer powders are sold under the names KSP-100®, KSP-101®, KSP-102®, KSP-103®, KSP-104® and KSP-105® by the company SHIN ETSU.

A composition according to the invention may comprise from 0.1% to 20% by weight, preferably from 1% to 10% by weight of filler(s), based on the total weight of said composition.

Colouring Materials

A composition according to the present comprises at least one or more colouring materials which may be selected from water-soluble or non-water-soluble, fat-soluble or non-fat-soluble, organic or inorganic colouring materials, optical effect materials, and mixtures thereof.

In the context of the present invention, colouring material means a compound capable of producing a coloured optical effect when formulated in sufficient quantity in a suitable cosmetic medium.

According to a particular embodiment, the colouring material(s) is (are) in particular selected from mineral and/or organic pigments, composite pigments (based on mineral and/or organic materials), dyes, nacres or pearlescent pigments, and mixtures thereof.

Preferably, the colouring materials are pigments.

Pigments should be understood to mean white or coloured inorganic (mineral) or organic particles, insoluble in the liquid organic phase in which they are dispersed, intended to colour and/or opacify the composition and/or the deposit made with the composition.

Among mineral pigments, mention may be made, by way of examples, of titanium dioxide (rutile or anatase), optionally surface-treated; black, yellow, red and brown iron oxides; manganese violet; ultramarine blue; chromium oxide; hydrated chromium oxide and ferric blue.

Examples of organic pigments are D&C Red No. 19; D&C Red No. 9; D&C Red No. 22; D&C Red No. 21; D&C Red No. 28; D&C Yellow No. 6; D&C Orange No. 4; D&C Orange No. 5; D&C Red No. 27; D&C Red No. 13; D&C Red No. 7; D&C Red No. 6; D&C Yellow No. 5; D&C Red No. 36; D&C Red No. 33; D&C Orange No. 10; D&C Yellow No. 6; D&C Red No. 30; D&C Red No. 3; D&C Blue 1; carbon black and cochineal carmine-based lacquers.

Among water-soluble dyes, mention may be made of Yellow 5, Yellow 6, Blue 1, Green 5, Green 3, Green 6, Orange 4, Red 4, Red 21, Red 22, Red 27, Red 28, Red 33, Red 40, cochineal carmine (CI 15850, CI 75470).

The fat-soluble dyes are for example Sudan Red, D&C Red 17, D&C Green 6, beta-carotene, soybean oil, Sudan Brown, D&C Yellow 11, D&C Violet 2, D&C Orange 5, quinoline yellow, annatto.

The nacres or pearlescent pigments may be selected in particular from white nacreous pigments, such as mica coated with titanium oxide, bismuth oxychloride; and coloured nacreous pigments, such as titanium mica with iron oxides, titanium mica with ferric blue or chromium oxide, titanium mica with an organic pigment of the aforementioned type, as well as bismuth oxychloride-based pigments. Mention may be made of the REFLECKS®, RONASTAR®, TIMIRON® and SYNCRISTAL® ranges of commercial nacreous pigments.

Advantageously, the colouring materials and in particular the pigments are surface treated with at least one hydrophobic or lipophilic treatment agent for better dispersion in the oil phase. The hydrophobic treatment agent is selected in particular from the group consisting of silicone surfactants; fluorinated surfactants; fluorosilicone surfactants; metal soaps, N-acylated amino acids or salts thereof; lecithin and derivatives thereof; isopropyl trisostearyl titanate; diisostearyl sebacate; natural vegetable or animal waxes, polar synthetic waxes; fatty esters; phospholipids, and mixtures thereof.

In particular, the colouring materials(s) is/are present in the composition in a content ranging from 2% to 30% by weight, preferably from 4% to 15% by weight based on the total weight of the composition.

According to a particular embodiment, the composition of the invention comprises pigments, in particular mineral pigments in a content ranging from 5 to 25%, in particular from 10 to 20% by weight based on the total weight of the composition.

Galenical Form

The composition is preferentially intended to be applied to the skin, in particular the skin of the face and/or neck, and is preferably in the form of an oil-in-water, water-in-oil or water-in-silicone emulsion. Preferably, it will be a water-in-oil emulsion, in particular a water-in-silicone emulsion which is the preferred form.

The composition is for example in the form of a facial fluid, a foundation, a foundation base, a finisher. Preferably, it is a face make-up composition, in particular a foundation.

The composition of the invention may further comprise any additive customarily used in cosmetics, such as UV filters, antioxidants, surfactants, gelling agents, preservatives, film-forming polymers, fragrances, cosmetic active agents, such as for example emollients, moisturizers, vitamins, anti-ageing agents, lightening agents, and mixtures thereof.

Cosmetic Process

The invention also relates to a cosmetic make-up process for keratinous materials, in particular the skin, preferably the skin of the face and/or of the neck, comprising applying to said keratinous material at least one cosmetic composition as defined previously in the invention.

In particular, the process is intended to give the skin a long-lasting skin-perfecting effect and a natural glow to the complexion.

The invention will be illustrated in the following non-limiting examples. Unless otherwise indicated, % are expressed as % by weight based on the total weight of said composition.

EXAMPLES

Example 1: Selection of Phenylated Silicone Oil According to the Invention

Different gloss oils were tested in a composition according to the invention in the form of a water-in-silicone emulsion in which the aqueous phase comprises a water-soluble film-forming polymer (VP/VA COPOLYMER), the oil phase comprises silicone oils and a fat-soluble film-forming polymer (ACRYLATES/DIMETHICONE COPOLYMER), and hydrophobically-treated pigments (titanium dioxide and iron oxides).

The compositions are prepared at room temperature according to the following protocol:

- in a main beaker, phases A1, A2 and A3 are mixed under stirring (Ultra-Turrax);
- in a secondary beaker, phase B1 is Rayneri stirred to obtain a homogeneous phase; phase B2 is then introduced under Rayneri stirring to homogenize the mixture of phases B1 and B2; phase B3 is then added to this mixture under Rayneri stirring just before emulsifying;
- phase B is emulsified in phase A under Rayneri stirring by gradually increasing the speed to 900 rpm for 15 minutes.

The compositions are then evaluated after application on the skin for their 'non-sticky' effect and their 'glow effect' otherwise known as 'healthy glow or natural radiance effect'.

TABLE 1

| Phase | Ingredients (INCI Name) | Test 1 Example according to the invention | Test 2 (comparative) | Test 3 (comparative) | Test 4 (comparative) |
|---|---|---|---|---|---|
| A1 | PEG-9 Polydimethylsiloxyethyl Dimethicone | 2 | 2 | 2 | 2 |
| | Dimethicone 5cs (volatile oil) | 14 | 14 | 14 | 14 |
| | Methyl Trimethicone (And) Acrylates/Dimethicone Copolymer (KP-549 ® from Shin Etsu) | 8% (of which 3.2% a.m.*) | 8% (of which 3.2% a.m.*) | 8% (of which 3.2% a.m.*) | 8% (of which 3.2% a.m.*) |
| | Isododecane (And) Disteardimonium Hectorite (and) Propylene Carbonate (BENTONE GEL ISD V ® from Elementis) | 8 | 8 | 8 | 8 |
| | Ethylhexyl Methoxycinnamate | 3 | 3 | 3 | 3 |
| | Trimethyl Pentaphenyl Trisiloxane (PH-1555 HRI from Dow Corning) | 5 | | | |
| | Phenylpropyldimethylsiloxysilicate (SILSHINE 151 ® from Momentive) | | 5 | | |
| | Diisostearyl Malate (HAIMALATE DIS ® from Kokyu alcohol kogyo co, ltd) | | | 5 | |
| | Phenyl Trimethicone 30 Cps | | | | 5 |
| A2 | Titanium Dioxide (CI77891) (And) Sodium Myristoyl Glutamate (And) Aluminium Hydroxide | 10.35 | 10.35 | 10.35 | 10.35 |
| | Iron Oxides (Red CI77491, Yellow CI77492 and Black CI77499) (And) Sodium Myristoyl Glutamate (And) Aluminium Hydroxide | 1.75 | 1.75 | 1.75 | 1.75 |
| | Peg-9 Polydimethylsiloxyethyl Dimethicone | 2 | 2 | 2 | 2 |
| | Methyl Trimethicone (volatile oil) | 7 | 7 | 7 | 7 |

TABLE 1-continued

| Phase | Ingredients (INCI Name) | Test 1 Example according to the invention | Test 2 (comparative) | Test 3 (comparative) | Test 4 (comparative) |
|---|---|---|---|---|---|
| A3 | Vinyl Dimethicone/Methicone Silsesquioxane Crosspolymer (KSP-100 ® from Shin Etsu) | 2 | 2 | 2 | 2 |
| B1 | Water | QS 100 | QS 100 | QS 100 | QS 100 |
| | Glycols | 8 | 8 | 8 | 8 |
| | Phenoxyethanol | 0.3 | 0.3 | 0.3 | 0.3 |
| | Tetrasodium EDTA | 0.1 | 0.1 | 0.1 | 0.1 |
| B2 | VP/VA Copolymer (Ashland PVP-VA S-630 ®) | 0.2 | 0.2 | 0.2 | 0.2 |
| B3 | Ethanol | 10 | 10 | 10 | 10 |
| | Evaluation of residual stickiness | Very slightly sticky | Sticky | Slightly sticky | Non-sticky |
| | Evaluation of the radiance/glow of the deposit | +++ | + | ++ | + |

a.m. = active material or dry extract
+++ = strong glow effect of the deposit
+ = weak glow effect of the deposit The result is that the phenylated silicone oil of formula (I) according to the invention, in particular Trimethyl pentaphenyl trisiloxane, in a composition as defined according to the invention, presents the best results on the criterion of the radiance of the deposit (glow effect, radiant complexion) without a sticky effect, compared with the other oils tested, in particular the other silicone oils or resins with a phenyl group.

The composition according to the invention (test 1) is also evaluated for its wear over time, in particular its wear at 24 h, under alternating heat/humidity conditions according to the following protocol:

- the composition is applied to the face at TO and a photograph is taken of the face at TO;
- the subject is then subjected to alternating heat (average temperature 25.8° C.)/humidity (average hygrometry 69%) conditions for 10 minutes, every two hours until T10 h (i.e., at T2 h, T4 h, T6 h, T8 h, and T10 h), then a photograph of the face is taken at T12 h and then another photograph of the face at T24 h;
- photographs taken at TO, T12 h and T24 h are compared.
- The result is that the composition of the invention meets our expectations: the make-up result lasts up to 24 h.

Example 2: Example Formulations

The following example formulations are non-limiting illustrations of the invention. The compositions are prepared according to the protocol described in Example 1.

Long-Lasting Foundation with Glow Effect

TABLE 2

| Phase | Ingredients (INCI Name) | % |
|---|---|---|
| A1 | PEG-9 Polydimethylsiloxyethyl Dimethicone | 2 |
| | DIMETHICONE (Volatile silicone oil) | 5 |
| | Isododecane (And) Acrylates/Polytrimethylsiloxymethacrylate Copolymer (FA 4004 ® ID SILICONE ACRYLATE from Dow Corning) | 8% (of which 3.2% a.m.) |
| | Isododecane (And) Disteardimonium Hectorite (And) Propylene Carbonate (BENTONE GEL ISD V ® from Elementis) | 8 |
| | Ethylhexyl Methoxycinnamate | 3 |

TABLE 2-continued

| Phase | Ingredients (INCI Name) | % |
|---|---|---|
| | Trimethyl Pentaphenyl Trisiloxane (Dow Corning PH-1555 HRI ®) (Non-volatile Phenyl Silicone Oil) | 5 |
| A2 | Titanium Dioxide (CI77891) (And) Sodium Myristoyl Glutamate (And) Aluminium Hydroxide | 10.35 |
| | Iron Oxides (Red CI77491, Yellow CI77492 And Black CI77499) (And) Sodium Myristoyl Glutamate (And) Aluminium Hydroxide | 1.75 |
| | PEG-9 Polydimethylsiloxyethyl Dimethicone | 2 |
| | Methyl Trimethicone (Volatile Silicone Oil) | 14 |
| A3 | Methylmethacrylate Crosspolymer | 1 |
| B1 | Water | QS 100 |
| | Glycols | 8 |
| | Phenoxyethanol | 0.3 |
| | Tetrasodium EDTA | 0.1 |
| B2 | VP/VA Copolymer (PVP-VA S-630 De Ashland) | 0.2 |
| B3 | Ethanol | 10 |

This foundation in the form of a water-in-silicone emulsion is prepared as described in Example 1. When applied to the skin of the face, it makes it possible to obtain a long-lasting (24 h) make-up with a skin-perfecting effect, the sensation of bare skin, and a natural glowing complexion thanks to the presence of this phenylated silicone oil and moisturizing agents (glycols).

Skin-Perfecting Foundation

TABLE 3

| Phase | Ingredients (INCI Name) | % |
|---|---|---|
| A1 | PEG-9 Polydimethylsiloxyethyl Dimethicone | 2 |
| | Dimethicone (volatile silicone oil) | 5 |
| | Methyl Trimethicone (And) Acrylates/Dimethicone Copolymer (KP-549 ® from Shin Etsu) | 8 (of which 3.2 a.m.) |
| | Isododecane (And) Disteardimonium Hectorite (And) Propylene Carbonate (BENTONE GEL ISD V ® from Elementis) | 8 |
| | Ethylhexyl Methoxycinnamate | 3 |
| | Trimethyl Pentaphenyl Trisiloxane (PH-1555 HRI ® from Dow Corning) (non-volatile phenylated silicone oil) | 4 |
| | Phenyl Trimethicone 30 cps | 5 |

TABLE 3-continued

| Phase | Ingredients (INCI Name) | % |
|---|---|---|
| A2 | Titanium Dioxide (CI77891) (And) Sodium Myristoyl Glutamate (And) Aluminium Hydroxide | 10.35 |
| | Iron Oxides (Red CI77491, Yellow CI77492 and Black CI77499) (And) Sodium Myristoyl Glutamate (And) Aluminium Hydroxide | 1.75 |
| | PEG-9 Polydimethylsiloxyethyl Dimethicone | 2 |
| | Methyl Trimethicone (volatile silicone oil) | 11% |
| A3 | Vinyl Dimethicone/Methicone Silsesquioxane Crosspolymer (KSP-100 ® from Shin Etsu) | 3% |
| B1 | Water | QS 100 |
| | Glycols | 8 |
| | Phenoxyethanol | 0.3 |
| | Tetrasodium EDTA | 0.1 |
| B2 | Polyvinylpyrrolidone (PVP K30 ® from SIGMA-ALDRICH) | 0.5% |
| B3 | Ethanol | 10 |

This foundation in the form of a water-in-silicone emulsion is prepared as described in Example 1. When applied to the skin of the face, it makes it possible to obtain a long-lasting (24 h) make-up with a skin-perfecting effect, the sensation of bare skin, and a natural radiant complexion.

The invention claimed is:

1. A cosmetic make-up composition in the form of a water-in-oil emulsion for keratinous materials, in the form of an emulsion, comprising, in a physiologically acceptable medium, at least:

a) trimethyl pentaphenyl trisiloxane, b) a fat-soluble film-forming polymer selected from the group consisting of silicone acrylate polymers selected from acrylate/dimethicone copolymers and acrylate/polytrimethylsiloxy-methacrylate copolymers, c) a water-soluble film-forming polymer selected from polyvinylpyrrolidone/vinyl acetate (PVP/VA) copolymer, and d) colouring materials which are pigments, and further comprising at least one soft-focus effect filler, one or more volatile oils selected from dimethicone, methyl trimethicone, isododecane and mixtures thereof, and at least one water-soluble solvent selected from $C_1$-$C_5$ lower monoalcohols, and wherein the at least one soft-focus effect filler is present in a content ranging from 0.1 to 20% by weight, based on the total weight of said composition, and wherein said pigments are present in a content ranging from 10 to 25% by weight, based on the total weight of said composition.

2. The cosmetic composition as claimed in claim 1, wherein it the one or more volatile oils is selected from methyl trimethicone, and mixtures of methyl trimethicone and (i) dimethicone and/or (ii) isododecane.

3. The cosmetic composition as claimed in claim 1, wherein the trimethyl pentaphenyl trisiloxane is present in the composition in a content ranging from 1 to 12% by weight, based on the total weight of said composition.

4. The cosmetic composition as claimed in claim 1, wherein it further comprises a second phenylated silicone oil, distinct from trimethyl pentaphenyl trisiloxane.

5. The cosmetic composition as claimed in claim 1, wherein the fat-soluble film-forming polymer b) is present in a content ranging from 1 to 7% by weight based on the total weight of said composition.

6. The cosmetic composition as claimed in claim 1, wherein the water-soluble film-forming polymer c) is present in a content ranging from 0.05 to 2% by weight based on the total weight of the composition.

7. The cosmetic composition as claimed in claim 1, wherein it is a face make-up composition.

8. A cosmetic make-up process for keratinous materials, comprising applying to said keratinous material at least one cosmetic composition as defined in claim 1.

9. The cosmetic composition as claimed in claim 1, wherein:

the trimethyl pentaphenyl trisiloxane a) is present in a content ranging from 3 to 8% by weight, based on the total weight of said composition, the fat-soluble film-forming polymer b) is present in a content ranging from 2 to 5% by weight, based on the total weight of said composition, the polyvinylpyrrolidone/vinyl acetate (PVP/VA) copolymer c) is present in a content ranging from 0.1 to 1% by weight, based on the total weight of said composition, the one or more volatile oils are present in a content ranging from 15 to 25% by weight based on the total weight of said composition, and the one or more water-soluble solvent is present in a content ranging from 10 to 25% by weight based on the total weight of said composition.

* * * * *